(12) United States Patent
Apperson et al.

(10) Patent No.: US 11,123,014 B2
(45) Date of Patent: Sep. 21, 2021

(54) SYSTEMS AND METHODS FOR AMBIENT ENERGY POWERED PHYSIOLOGICAL PARAMETER MONITORING

(71) Applicant: Stryker Corporation, Kalamazoo, MI (US)

(72) Inventors: Ryan W. Apperson, Bothell, WA (US); Reza Sharif, Redmond, WA (US); Matthew Lawrence Bielstein, Seattle, WA (US); Arthur T. Lounsbery, Woodinville, WA (US)

(73) Assignee: Stryker Corporation, Kalamazoo, MI (US)

( * ) Notice: Subject to any disclaimer, the term of this patent is extended or adjusted under 35 U.S.C. 154(b) by 297 days.

(21) Appl. No.: 15/927,749

(22) Filed: Mar. 21, 2018

(65) Prior Publication Data

US 2018/0271443 A1 Sep. 27, 2018

Related U.S. Application Data

(60) Provisional application No. 62/474,566, filed on Mar. 21, 2017.

(51) Int. Cl.
*A61B 5/02* (2006.01)
*A61B 5/00* (2006.01)
(Continued)

(52) U.S. Cl.
CPC ............ *A61B 5/6833* (2013.01); *A61B 5/002* (2013.01); *A61B 5/01* (2013.01); *A61B 5/021* (2013.01);
(Continued)

(58) Field of Classification Search
CPC .. A61B 5/01; A61B 5/02; A61B 5/021; A61B 5/022; A61B 5/024; A61B 5/02405; A61B 5/0245; A61B 5/053; A61B 5/0531; A61B 2560/02; A61B 2560/0204; A61B 2560/0209; A61B 2560/0214; A61B 2560/04; A61B 2560/0475; A61B 5/24; A61B 5/242; A61B 5/25; A61B 5/251;
(Continued)

(56) References Cited

U.S. PATENT DOCUMENTS

2011/0275907 A1* 11/2011 Inciardi ................. A61B 5/1112
600/301
2012/0029315 A1* 2/2012 Raptis .................. A61B 5/0022
600/301
(Continued)

*Primary Examiner* — Ahmed M Farah
(74) *Attorney, Agent, or Firm* — Lee & Hayes, P.C.

(57) ABSTRACT

A system for treating and/or monitoring a patient includes a patient physiological parameter monitoring patch and a companion device. The patient physiological parameter monitoring patch including an energy harvesting module, an energy storage module, a sensor module and a communication module. The energy harvesting module harvesting energy from one or more ambient sources, the energy being storable in the energy storage module and usable by one or more components of the patient physiological parameter monitoring patch. The sensor module senses one or more physiological parameters of the patient and the communication module can transmit the sensed data. The companion device can receive the sensed physiological parameters and can send the same to a remote device or store the same.

18 Claims, 4 Drawing Sheets

(51) Int. Cl.
*A61B 5/145* (2006.01)
*A61B 5/01* (2006.01)
*A61B 5/021* (2006.01)
*H02N 11/00* (2006.01)
*A61B 5/1455* (2006.01)
*A61B 5/0531* (2021.01)
*A61B 5/318* (2021.01)

(52) U.S. Cl.
CPC ......... *A61B 5/0531* (2013.01); *A61B 5/14539* (2013.01); *A61B 5/14551* (2013.01); *A61B 5/318* (2021.01); *A61B 5/746* (2013.01); *A61B 2560/0209* (2013.01); *A61B 2560/0214* (2013.01); *H02N 11/002* (2013.01)

(58) Field of Classification Search
CPC ......... A61B 5/256; A61B 5/257; A61B 5/318; A61B 5/33; A61B 5/683; A61B 5/6831; A61B 5/6832; A61B 5/6867; A61B 5/6869; A61B 5/72; A61B 5/002; A61B 5/0022; A61B 5/0024; A61B 5/0026; A61B 2562/04; A61B 2562/06; A61B 2562/22; A61B 2562/221; A61B 2562/225
USPC ....... 600/300, 301, 481, 485, 500, 508, 509, 600/519, 549
See application file for complete search history.

(56) References Cited

U.S. PATENT DOCUMENTS

| | | | |
|---|---|---|---|
| 2012/0203078 A1* | 8/2012 | Sze | G06F 19/3418 600/301 |
| 2015/0313496 A1* | 11/2015 | Connor | A61B 5/6814 600/301 |
| 2016/0346584 A1* | 12/2016 | Schneider | A61B 5/0024 |
| 2017/0258585 A1* | 9/2017 | Marquez | A61F 2/2412 |
| 2020/0006988 A1* | 1/2020 | Leabman | H02J 50/80 |

* cited by examiner

SYSTEMS AND METHODS FOR AMBIENT ENERGY POWERED PHYSIOLOGICAL PARAMETER MONITORING

CROSS-REFERENCE TO RELATED APPLICATIONS

This patent application claims the benefit of and priority to U.S. Provisional Patent Application Ser. No. 62/474,566, filed on Mar. 21, 2017, entitled "Harvesting various sources of ambient energy for powering wireless Vital Sign Patch (VSPs) and sensor networks and applications," the contents of which are hereby incorporated by reference in their entirety.

BACKGROUND

The collection and/or monitoring of physiological data is an important aspect of patient healthcare. Patient physiological data can provide insight into the health and well-being of an individual and provide indication of potential physiological distress. Typically, multiple different medical devices and/or machines are used with each device capturing data regarding a single or sometimes multiple physiological parameters or characteristics. These monitoring systems can be distressing in their own right to the individual connected to the medical device, often causing the individual to experience some level of discomfort.

Additionally, the medical devices can require support for their services, such as connections, such as cords or cables, for data transmission and/or power and/or other resources. These connections can limit the mobility and/or use of the medical device as it can be constrained by its support requirements. Constraints, such as these and/or others, can also contribute to the discomfort of the individual due to the decreased range of motion and/or limited movement allowed by the individual while connected to various medical devices and/or monitors.

To assist with the mobility issue, some medical devices and/or monitors include power supplies, such as batteries, that allow the device to move with the user. The various cables connecting the monitoring device to one or more sensors still constrain the available motion allowed the individual although the self-powered systems are more portable. However, even for wireless systems, the patient's motion can still be constrained due to the power requirements of the device. For example, conventional devices include batteries to supply power to device, however, the batteries can require recharging and/or replacement at intervals. This battery dependency limits the range and/or mobility of the patient connected to the device because of the need to carry additional batteries and/or travel within a predetermined distance relative to a recharging station. The battery dependency is also expensive and can be unreliable. As such, many patient physiological parameter monitoring systems and/or devices reduce the mobility and/or range of motion of an individual being monitored.

There exists a need for systems and/or methods that improve the collection and/or monitoring of patients.

DETAILED DESCRIPTION

Figure 1:
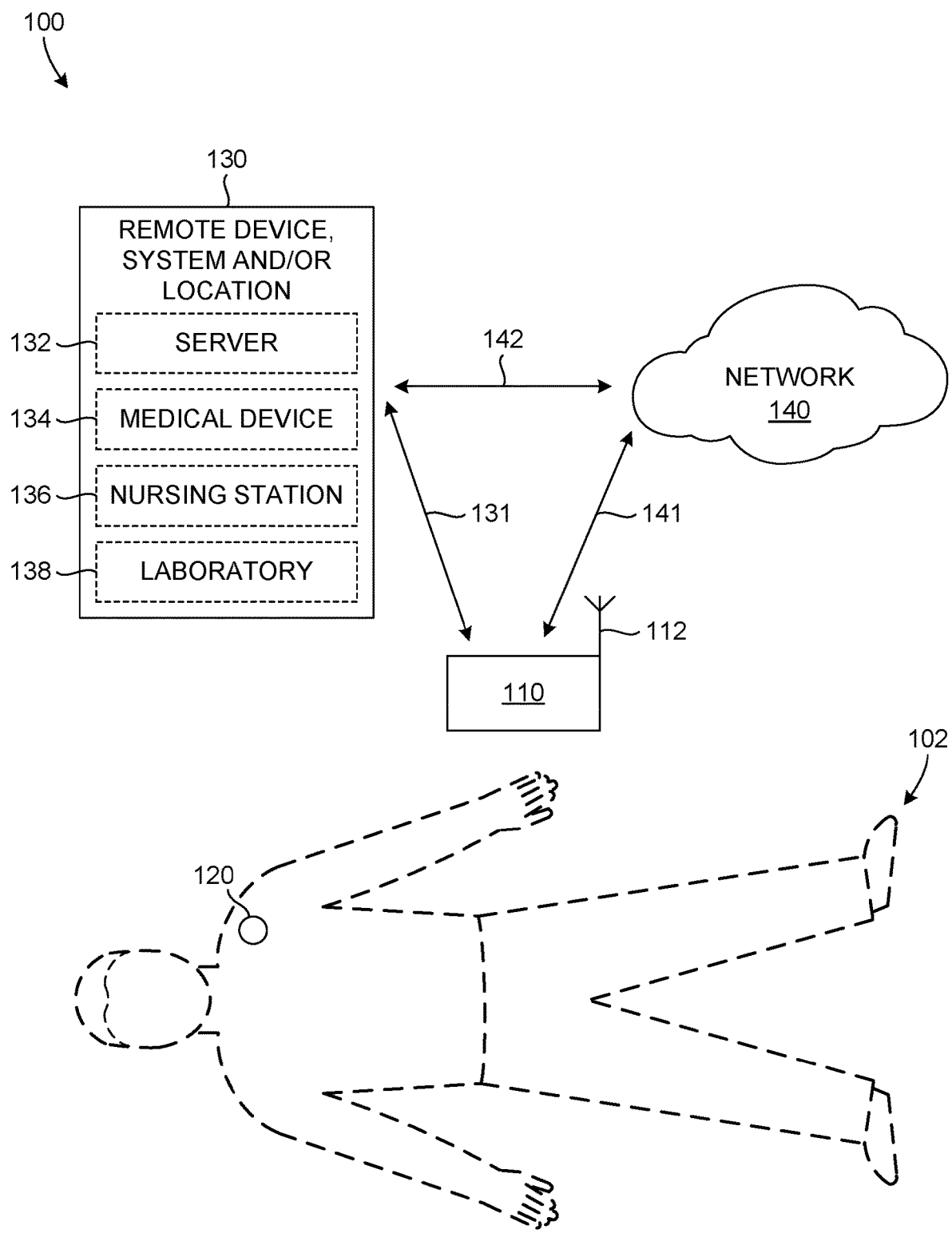
FIG. 1 illustrates an example ambient energy powered physiological parameter monitoring system.

Physiological parameter data collection and/or monitoring systems and/or methods are described below. The system includes a sensor containing element, such as a patch, that can be mounted directly to, or placed on, an individual to monitor and collect data regarding one or more physiological parameters and/or characteristics of the individual. The sensor can obtain power, such as electrical energy, from an included energy harvesting module that can provide power in response to being exposed to ambient energy sources, such as radio transmissions, light, heat and/or other energy sources. Obtaining energy from ambient energy sources allows the sensor and/or patch to perform various functions without the need to be coupled physically to a power source, such as by a wire or cord. The wireless powering of the sensor containing element and/or patch, can allow the individual increased range of motion and increased movement distances due to the lack of a directly coupled power source. In addition, the sensor containing element can include an energy storage device to allow the element to capture electrical energy, such as from the ambient energy source(s), and store the electrical energy to provide electrical power for one or more functions and/or features of the device.

The ambient energy can be provided by a companion device, in some examples, that can be located proximally to the sensor containing element. The companion device generates an electrical field, such as short-range radio transmissions, or other electromagnetic radiation, that can be the ambient energy source from which the sensor containing element can derive or obtain power. The companion device can be carried by the individual to provide the ambient energy source for the sensor containing element. Alternatively, the companion device, or the ambient energy source providing functionality thereof, can be integrated with one or more other devices, such as a monitoring device or cellphone. These other devices can be mobile and can move with the individual, such as being carried on the person of the individual, or the other devices can be stationary. The mobile device can be located proximal to the individual due to it being able to move with the individual. The stationary devices cannot move with the individual but can provide the functionality of the companion device, or ambient energy source, while the individual is within range of the stationary device. Multiple stationary devices can be located within a location so that as the individual moves around the location they remain located within range of one or more of the stationary devices. Alternatively, the individual can move outside of the range of the stationary, or other device, and once the individual is within range of the same, or another, device the sensor containing element can be energized.

For example, a patient can be in a hospital bed that can include the ambient energy source functionality by radiating electromagnetic energy from which the sensor containing element can derive, or obtain, electrical energy therefrom. The electromagnetic radiation can be generated to purposely provide the ambient energy source for the sensor containing element and/or can be generated for other purposes/functions, or inadvertently, and the sensor containing element can scavenge, or obtain, electrical energy from such an ambient energy source. In an embodiment, a "smart" hospital bed can purposely generate and transmit electromagnetic radiation, such as radio frequency radiation, to provide an ambient energy source for the sensor containing element. Additionally, or alternatively, the "smart" hospital bed can generate and radiate electromagnetic radiation for the communications, such as emitting a wireless communication signal. The sensor containing element can receive this transmitted electromagnetic radiation, generated to facilitate communication, and can scavenge, or obtain electrical energy from such electromagnetic radiation. The ability, structure and/or functionality of the sensor containing element to derive, or obtain, power from ambient energy sources can allow the sensor containing element to receive necessary electrical energy for the one or more functions/features of the sensor containing element without physically coupling the sensor containing element to a power source, such as by a wire or cord. In another embodiment, or in conjunction with scavenging intentional radiation, the sensor element may also scavenge electrical energy that is emitted unintentionally from electronic devices that is available in the sensors environment.

Physiological data collected by the sensor containing element can be transmitted from the sensor, or device/system coupled thereto, to the companion device, or base station, that can collect, aggregate, monitor, analyze, and/or transmit the collected physiological data to one or more remote devices, systems and/or users. The companion device can receive, process and/or analyze the received physiological data and can initiate a response accordingly. For example, the companion device can monitor the received physiological data for abnormalities, such as physiological data outside of a threshold(s), and/or trends. In response to the monitoring, processing and/or analysis of the physiological data, the companion device can initiate one or more responses, such as altering the collection of the physiological data, transmitting the received physiological data and/or transmitting an alert or notification to one or more remote devices, systems and/or users. Remote devices, systems and/or user can include additional medical devices, such as a defibrillator/monitor, that can be coupled to and/or monitoring the physiological state of the individual. Additionally, the remote devices/systems can include one or more data repositories, or databases, storing information related to the individual. Other remote systems can include a patient monitoring and/or tracking system that can aggregate information regarding a patient from one or more sources and can present and/or provide such information to one or more devices, systems and/or users. Alternatively, the sensor containing element can transmit collected physiological data directly to one or more remote devices, systems and/or users. In addition to the remote device, system and/or user, the physiological data can also be transmitted to the companion device.

In an example, in response to a trend indicating a decrease in a state of one or more monitored physiological parameters, the companion device can request additional information from a remote device, system and/or user and/or can request additional, and/or different, physiological data from one or more sensor containing elements monitoring one or more physiological parameters and/or characteristics of the individual. Additionally, or alternatively, the companion device can alter the collection of the physiological data, such as increasing a sampling frequency of the physiological data from the sensor containing element which can include longer monitoring periods, more frequent monitoring periods, and/or real-time transmission of sensed physiological data. Based on the physiological data received, the companion device can cause treatment and/or intervention to be administered to the individual by a device system and/or user. For example, the individual can be monitored by the companion device and the sensor containing element and also coupled to a treatment device, such as defibrillator or other medical device. In response to a physiological state, based on the received physiological data, the companion device can communicate to the coupled treatment device to cause the coupled treatment device to initiate treatment to the individual. Additionally, the companion device can be connected to and/or can include a power source to allow the companion device to generate and/or transmit at least a portion of the ambient energy that is received by the sensor to provide electrical power for the sensor and its operation. Such treatment and/or intervention can be initiated by the companion device, and/or a remote device/system that receives the physiological data, without the intervention of the individual or another to provide or initiate the treatment/intervention.

The sensor containing element can sense physiological data of the individual in a continuous, a scheduled, or an "on-demand" manner. Physiologic data can be sensed and/or collected continuously by the sensor containing element, sensed and/or collected based on a schedule, and/or sensed and/or collected when prompted by a user, or other device/system. The collected data can similarly be transmitted from the sensor containing element, in a continuous, scheduled and/or an "on-demand" manner. The companion device can control the sensor containing element to control the sensing, collection and/or transmittal of the physiological data by the sensor containing device. Alternatively, the sensor containing device can control all or a portion of the sensing, collection and/or transmittal of the physiological data.

The system of the sensor containing element and companion device provides a wireless system in which power and data can be communicated between the sensor containing element, the companion device and/or one or more other devices, systems and/or users. Such a system can be used to monitor an individual in multiples settings, or environments, such as at a residence or workplace, as may be typical for the individual, and/or at an emergency or other treatment setting. The system can provide physiological data to guide various monitoring and/or treatment of the patient in one or more of the environments and/or settings. Additionally, the collection of the physiological data can be modified and/or altered based on the individuals setting or environment. Further, the system can continue to provide physiological data as the individuals setting and/or environment changes, such as the individual might experience during a medical event. Prior to the event, the individual's physiological state can be monitored by the system which can transmit an alarm in response to a change in the physiological state of the individual. The physiological state change can cause the individuals setting/environment to change from a residential setting to a hospital setting where the individual may be transported to receive treatment in response to the alarm and/or physiological state change. While at the hospital, the system can continue to provide physiological data regarding the individual. The hospital setting can include additional and/or different companion devices, or other devices/systems providing at least a portion of similar functionality, that can interface with the sensor containing element on the individual to collect physiological data.

FIG. 1 is an example ambient energy powered physiological parameter monitoring system 100 in-use with a patient or wearer 102. The patient or wearer 102 has a physiological parameter monitoring patch 120 place thereon. The patch 120 includes one or more sensors for monitoring one or more physiological parameters and generating an output based on the one or more physiological parameters. Electrical energy for powering the various functions and/or features of the patch 120 can be provided wirelessly from radio energy, or transmissions, from a companion device 110. The companion device can include an antenna, transmitter and/or transceiver for broadcasting a power signal to the patch 120. The power signal can have various properties and/or characteristics that can be selected or shaped to assist with the efficient transmission and conversion of the power signal into electrical energy by the patch 120. The companion device 110 can also include an antenna 112 for receiving data from the patch 120, such as physiological parameter data from the one or more sensors of the patch 120.

The companion device 110 can also be communicatively coupled 141 to a network 140 for transmitting collected physiological data thereto. The network 140 can be further communicatively coupled 142 to one or more remote devices, systems and/or locations 130, such as a server 132, medical device 134, nursing station 136, laboratory 138 and/or other remote device, system and/or location. Physiological data from the companion device 110 can be routed and/or transmitted to the one or more remote devices, systems and/or locations via the network 140. Additionally, the communication can be two-way to allow the remote device, systems and/or locations to communicate with the companion device 110, such as to provide instructions and/or other data to alter the collection and/or analysis of the physiological data.

The companion device 110 can be communicatively coupled 131 to one or more remote device, system and/or location 130, such as the server 132, medical device 134, the nursing station 136, the laboratory 138, and/or other remote devices, systems and/or locations. The companion device 110 can transmit physiological data and/or other communications, such as instructions, to the one or more remote devices, systems and/or locations 130. The instructions can cause one or more of the remote devices, systems and/or locations to output a response, such as a treatment by the medical device 134 that is administered to the patient 102. The communications from the companion device 110 to the one or more remote devices, system and/or locations 130 can also include an alert or notification issued by the companion device 110 based on the collected physiological data and/or the review/analysis of the collected physiological data.

In another embodiment, the power signal can be broadcasted and/or transmitted by another device/system. The other device/system can be connected to and/or can have a power source to generate and/or transmit the power signal. In an example, the patient 102 can be in a bed that includes a power transmitter that transmits the power signal to the one or more patches 120 on the patient 102 to provide the electrical energy necessary for their features and/or functions. The power signal transmission ability can be integrated in other alternative devices and/or systems which can provide the power signal and/or can provide additional power signals to assist with providing power to the patches 120.

The patch 120 can also include a unique identifier, such as an encoded identity and/or a specific broadcast frequency, or range, associated with a particular patch 120. The physiological data transmitted by the patch 120 to the companion device 110 can include the unique identifier associated with the patch 120 to allow the companion device 110 to identify the transmitter of the physiological data. This can allow a single companion device 110 to communicate with, or monitor, one or more patches 120 on one or more patients 102. Additionally, the unique identifier for the patch 120 can be further stored at a remote device/system to allow one or more companion devices 110 to determine the identity of the patch 120 and/or associate received physiological data with a particular patient 102. This organization can allow a patient 102 to be moved through a system and/or facility while allowing for the continued collection of physiological parameter data via multiple companion devices 110 the patient 102 is proximal to as the patient 102 is transported or moved.

In an embodiment, the collection of physiological data by the patch 120 can be initiated by the reception of ambient energy, such as the power signal, from the companion device 110. The companion device 110 can continue to provide ambient energy until the physiological data from the patch 120 is received by the companion device 110. In this manner, the broadcast of ambient energy by the companion device 110 causes the collection of the physiological data. Cycling the broadcast of ambient energy by the companion device 110 can be used to regularly collect physiological data from the patient 102 via the patch 120. In an embodiment in which multiple patches 120 are placed on a patient 102 to monitor one or more physiological parameters, the patches 120 associated with a particular physiological parameter can be associated with a particular characteristic of the broadcast power signal. For example, first patches 120 associated with monitoring patient 102 temperature can be attuned to receive, or harvest, energy from radio transmissions of a particular first frequency, or first range of frequencies. Second patches 120 associated with monitoring patient 102 oxygen saturation (SpO2) can be attuned to receive, or harvest, energy from radio transmissions of a particular second frequency, or second range of frequencies. This can allow the companion device 110 to collect data for a particular physiological parameter individually. The companion device 110 can broadcast a power signal at the first frequency, or first range of frequencies, to provide power to the first patches to collect first physiological data and/or transmit first physiological data and then the companion device 110 can broadcast a power signal at the second frequency, or second range of frequencies, to provide power to the second patches to collect and/or cause the transmission of second physiological data.

In another embodiment, the companion device 110 can continuously broadcast ambient energy to allow the patch 120 to collect physiological data and/or the patch 120 can harvest ambient energy from the environment about the patch 120 to allow for the collection of physiological parameter data by the patch 120. To receive the physiological data, the companion device 110 can transmit a signal, such as a communication signal or a predetermined power signal, to cause the patch 120 to transmit the physiological data and/or collected physiological data.

The companion device 110 of FIG. 1 is shown remote from, and/or proximal to, the patient 102. In other embodiments, the companion device 110 can be worn and/or placed on the body of the patient 102. For example, a harness can be worn by the patient 102 to constrain the companion device 110 to their body. In another example, the companion device 110 can be placed in the pocket of clothes of the patient 102. Other locations proximal to and/or on the patient 102 can also be used to constrain the companion device 110 to the patient 102 and allow for the radiation of ambient energy by the companion device 110 to the patch 120 and the collection of physiological data by the companion device 110 from the patch 120.

The companion device 110 can include predetermined physiological parameter trends and/or limits to cause the companion device 110 to perform one or more actions in response. The response can include transmitting an alert or notification to a remote device, system and/or user. Additionally, the companion device 110 can transmit at least a portion of the collected physiological data to a remoted device, system and/or user. The physiological data transmitted can include real-time physiological data from the patch 120 on the patient 102 and/or historical data and/or data trends collected and/or processed from previous collections of physiological data from the patch 120 by the companion device 110. For example, the companion device 110 can determine that a physiological parameter being monitored with the patch 120 has exceeded a threshold value and/or trend and can cause an alert to be transmitted. The alert can be directed to a remote user to allow the user to review the physiological data, such as the real-time physiological data and the historical data and/or data trends, to assist with in an assessment of the patient 102. The remote device, system and/or user can review the received physiological data and can perform various functions and/or responses as a result of the review, such as dispatching assistance to the patient 102 and/or a patient 102 treatment.

Figure 2:
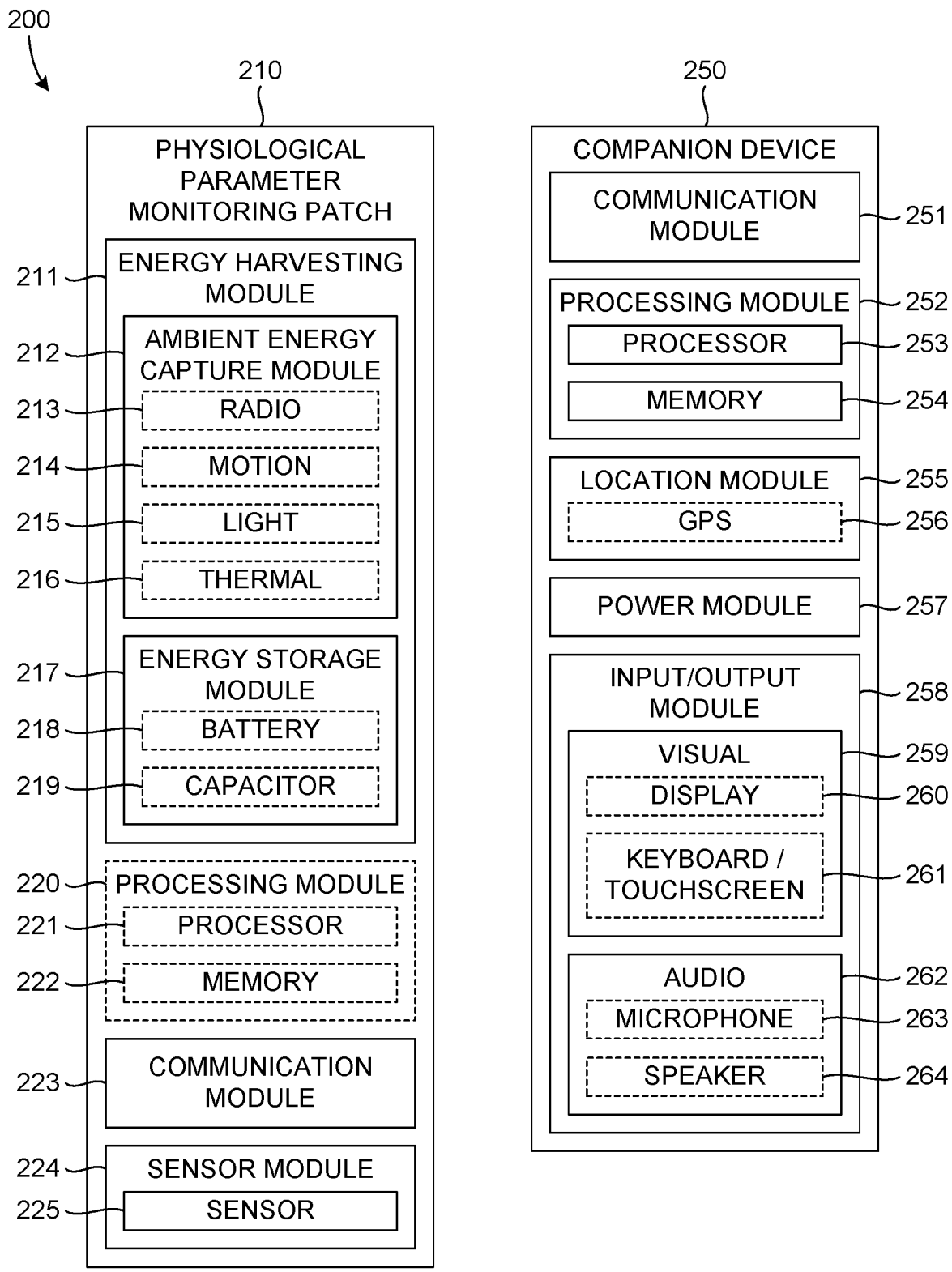
FIG. 2 illustrates a block diagram of an example ambient energy powered physiological parameter monitoring system.

FIG. 2 is an example block diagram of a system 200 for ambient energy powered physiological parameter monitoring. The system 200 includes a physiological parameter monitoring patch 210 that senses and/or monitors a patient's physiological parameter(s) and transmits the data to a companion device 250. The companion device 250 can process the data received from the physiological parameter monitoring patch 210 and/or can transmit the data received from the physiological parameter monitoring patch 210 to another device, system and/or user.

The physiological parameter monitoring patch 210 can be placed, or adhered, to a patient to monitor one or more physiological parameters of the patient. The patch 210 can include an energy harvesting module 211, an optional processing module 220, a communication module 223 and a sensor module 224. The sensor module 224 generates data based on the physiological parameter being monitored and that sensor data can be processed by the processing module 220 and/or transmitted from the patch 210 to an external device and/or system, such as the companion device 250, by the communication module 223. To provide power to the various functions and features of the patch 210, an ambient energy capture module 212 of the energy harvesting module can "harvest," or obtain energy, from one or more sources external to the patch 210. The "harvest" of energy is performed without the direct, physical connection of the patch to a power source. In addition to the ambient energy capture module 212, the energy harvesting module 211 can optionally include an energy storage module 217 to store and provide energy for the various functions and features of the patch 210.

The energy harvesting module 211 includes the ambient energy capture module 212 to gather, or harvest, energy to power the features and/or functions of the physiological parameter monitoring patch 210. Additionally, the energy harvesting module 211 can include the energy storage module 217 that can store energy collected by the ambient energy capture module 212 and/or can otherwise include stored energy. To provide the power necessary for the various functions and/or features of the physiological parameter monitoring patch 210, such as the sensing of the physiological parameter by the sensor module 224 and/or the transmission of the sensed physiological data by the communication module 223, the energy harvesting module 211 can be activated and/or energized.

The ambient energy capture module 212 can include one or more elements, devices, and/or system for gathering, or obtaining/capturing, ambient energy from the surroundings of the physiological parameter monitoring patch 210. Examples of ambient energy that the ambient energy capture module can collect are radio energy 213, motion energy 214, light energy 215 and/or thermal energy 216. Exposure of the ambient energy capture module 212 to radio waves, motion, light and/or thermal variations, can cause the one or more elements, devices, and/or systems of the ambient energy module 212 to capture, or salvage, energy from such exposure.

In an example, the radio energy 213 capture of the ambient energy capture module 212 can include one or more elements, device and/or systems for extracting, or capturing, energy from exposure to various radio transmissions. The ambient energy module 212 can include one or more antennas to receive the various radio transmissions and cause an induced current due to the exposure. The induced current caused by the exposure to the radio transmissions can be used to energize one or more features and/or functions of the physiological parameter monitoring patch 210 and/or stored by the energy storage module 217.

The radio transmissions to which the ambient energy capture module 212 is exposed can include one or more radio waves having various properties, such as a frequency, wavelength, amplitude, and/or other properties/characteristics. The periodic/cyclic nature of radio waves causes a current to be induced in one or more elements, devices, and/or systems, such as an antenna, of the ambient energy capture module 212. The element, device and/or system can be tuned and/or constructed to receive radio transmissions having a specific property/characteristic value/magnitude, or a range thereof.

The radio transmissions to which the ambient energy capture module 212 is exposed can be common radio transmissions, such as media broadcast signals, cellular phone transmissions, wireless internet signals and/or other sources of radio energy radiation. Additionally, or alternatively, the ambient energy capture module 212 can receive radio transmissions that are broadcasted or transmitted to provide power/energy to the physiological parameter monitoring patch 210 and/or other wireless power transmission purposed. In an example embodiment, the companion device 250, and/or other device/system can broadcast radio transmissions having properties/characteristics aligned with those that the ambient energy capture module 212 is attuned to receive. In this manner, the other device/system can effectively transmit and/or provide energy from the device/system to the physiological parameter monitoring patch 210 wirelessly.

The ambient energy capture module 212 can have multiple elements, devices and/or systems to capture energy from radio transmissions. For example, the ambient energy capture module 212 can include a first antenna to capture energy from first radio transmissions having a first frequency or range and a second antenna to capture energy from second radio transmissions having a second frequency or range. The energy captured from the first and second radio transmissions can be different, such as a first power captured from the first radio transmissions and a second, increased, power captured from the second radio transmissions. These various power captures can be used to provide energy or power to one or more functions and/or features of the physiological parameter monitoring patch 210. For example, the first power can be supplied to the sensor module 224 and/or memory 222 of the processing module 220 to collect and store physiological parameter data. The second power can be supplied to the communication module 223 to then transmit the stored physiological parameter data. In an example embodiment, the reception of second radio transmissions, and subsequent capture of the second power, can initiate the transmission of the physiological data. In this manner, the various functions and/or features of the physiological parameter monitoring patch 210 can be associated with one or more power/energy level/amount, with one or more features and/or functions activated/initiating and/or operating based on the level, or amount, of power/energy currently captured by the energy harvesting module 211 and/or capable of being supplied and/or supplemented by the energy storage module 217. The various power management functions of the patch 210 can be based on the electrical circuit layout and/or arrangement of the various features/functions and/or by a processor 221 of the processing module 220.

The ambient energy module 212 can also capture energy caused by motion 214 of the patch, such as by movement of a person upon which the patch is placed. The ambient energy module 212 can include one or more elements, devices, and/or systems for converting the motion, or kinetic energy, of the physiological parameter monitoring patch 210 into power/energy that can be supplied to the various features and/or functions of the patch 210 and/or stored by the energy storage module 217.

A mechanical element, device and/or system of the ambient energy module 212 can convert the mechanical motion of the physiological parameter monitoring patch 210 into electrical energy. The mechanical element, device and/or system can harvest the motion of the patch 210 and can be coupled to a generator, or electrical generating element, for converting the mechanical motion into electrical energy. For example, the ambient energy module 212 can include a magnet that is allowed to move within a coil of wire, as the magnet moves within the coil due to motion of the patch 210, a current is induced in the coil. The current can be supplied to various functions and/or features of the patch 210 and/or the energy storage module 217. In another example, the patch 210 can include a rotating weight/pendulum. Rotational energy, or motion, of the weight/pendulum, caused by motion of the patch 210, can be converted into electrical energy, such as by a generator.

Another element, device and/or system for converting motion into electrical energy can include the use of piezoelectric materials in the physiological parameter monitoring patch 210. Piezoelectric materials are a class, or group, of materials that generate an electrical charge when a stress is applied. For example, the bending of a piezoelectric material, such as by motion of the patch 210, can cause the piezoelectric material to generate an electrical charge that can be collected and/or used to power one or more functions/features of the patch 210 and/or the energy storage module 217. The piezoelectric material can be integrated, or included, with the patch 210 and/or can be an element of the patch 210.

Other suitable elements, devices and/or systems for converting mechanical motion of the physiological parameter monitoring patch 210 can be included in and/or coupled to the ambient energy capture module 212 to provide power/energy for one or more functions/features, and/or the energy storage module 217, of the patch 210. This can allow the ambient energy capture module 212 to capture, or obtain, electrical energy from the motion 214 of the patch 210.

Another source of ambient energy can include light 215 energy. Light 215 energy can include energy from one or both natural, such as the sun, and artificial light sources, such as overhead lighting. The light 215 can be in a visible portion of the spectrum, such as chromatic light, and/or can be in a non-visible portion of the spectrum, such as infrared light. The ambient energy capture module 212 can include one or more elements, devices and/or systems for receiving light 215 and generating energy/power therefrom. For example, the ambient energy capture module 212 can include a photovoltaic element that uses the photovoltaic effect to generate an electrical charge in response to being struck with, or receiving, light 215. The electrical energy derived from the light 215 can provide power for one or more functions/features of the physiological parameter monitoring patch 210 and/or the energy storage module 217. Other light 215 stimulated, energy generating elements, devices and/or systems can be included in the patch 210 to generate electrical power in response to the exposure to light 215.

A further source of ambient energy can include thermal 216 energy. Thermal 216 energy can include capturing, or obtaining, energy from the thermal state(s)/environment(s) about the physiological parameter monitoring patch 210. For example, the thermal 216 energy of a patient to which the patch 210 is affixed, can be used to generate power/energy for the various functions and/or features of the patch 210. Additionally, the thermal 216 energy of temperature fluctuations in the environment about the patch 210, such as ambient room temperature, can be used to generate power/energy.

Various elements, devices and/or systems can be used to convert thermal 216 energy received by the physiological parameter monitoring patch 210, and/or the ambient energy capture module 212, to electrical energy that can be supplied to the various features/functions of the patch 210 and/or the energy storage module 217. For example, one or more thermoelectric elements, or generators, can be included in the ambient energy captured module 212 and/or the patch 210. The thermoelectric elements generate electrical energy using the Seebeck effect due to the exposure of the thermoelectric elements to heat flux, or temperature differences. The thermoelectric elements can be arranged so that one side is exposed to the heat energy radiating from the patient or another heat source and the other side of the thermoelectric element is arranged to be exposed to a cooler environment, such as the ambient air. The temperature variation across the thermoelectric element generates electrical energy that can be supplied to various functions/features of the physiological parameter monitoring patch 210 and/or the energy storage module 217.

The ambient energy capture module 212 and/or the physiological parameter monitoring patch 210 can include one or more elements, devices and/or systems to capture, or obtain, energy from one or more sources, such as radio 213, motion 214, light 215 and/or thermal 216 sources. The ambient energy capture module 212 receives energy from the one or more sources to generate, or cause to be generated, electrical energy that can be supplied to the various functions and/or features of the patch 210 and/or the energy storage module 217.

The energy storage module 217 can include one or more energy storage elements, devices and/or systems, such as a battery 218 and/or a capacitor 219. The energy storage module 217 can store electrical energy, such as from the ambient energy capture module 212, an energy source external the physiological parameter monitoring patch 210 and/or an energy storage device that is included with and/or coupled to the patch 210.

The battery 218 can be included in the energy storage module 217 and can be a permanent or replaceable battery. The battery 218 can store and supply electrical energy to power the various functions/features of the physiological parameter monitoring patch 210. Additionally, the battery can be rechargeable, allowing the battery to store electrical energy from the ambient energy capture module 212, or other sources. In an example, the battery 218 can be included in the patch prior to use and contain at least a portion of an electrical charge to be able to provide electrical energy to the various features and/or functions of the patch 210. In the example, the battery 218 can also be chargeable/rechargeable to allow the ambient energy capture module 212 to transmit electrical energy to the battery 218 for storage. The battery 218 can also be included in the patch 210 and not include an electrical charge prior to use and the battery 218 can act as storage of electrical energy from the ambient energy capture module 212.

The battery 218 can provide electrical energy for and/or provide additional electrical energy for the various functions and features of the physiological parameter monitoring patch 210. For example, due to the lack of available ambient energy, the battery 218 can provide the necessary electrical energy for one or more functions/features of the patch 210. In another example, the electrical energy supplied by ambient energy capture module 212 may be insufficient for one or more functions/features of the patch 210 and the battery 218 can supply the additional electrical energy. For example, the ambient energy capture module 212 can be providing electrical energy necessary for the physiological parameter sensing, or data collection, such as by the sensor module 224, and additional, unneeded electrical energy can be stored in the battery 218. Certain functions/features of the patch 210, such as the transmission of the collected physiological parameter data, such as by the communication module 223, can require electrical energy beyond the immediate generational capabilities of the ambient energy capture module 212, the necessary electrical energy can then be supplied by the battery 218, which discharges the electrical energy stored previously from the electrical energy generated by the ambient energy capture module 212. The battery 218 can be pre-charged, charged, and/or recharged to supply electrical energy to one or more functions/features of the physiological parameter monitoring patch 210.

Additionally, the ability of the battery 218 to act as a storage for electrical energy can also be used to buffer the energy generated, or obtained, by the ambient energy capture module 212. For example, the ambient energy capture module 212 can output electrical energy with a time varying characteristic, such as a current. The time varying nature of the output electrical energy, such as voltage spikes, can be potentially damaging to components/systems of the patch 210. The battery 218 can store and/or supplement the electrical energy supplied to the various functions/features of the patch 210 to prevent damage to the various components/systems of the patch 210 and to enable the components/systems to function during dips, or lulls, in the electrical energy supplied by the ambient energy capture module 212.

The energy storage module 217 can also include a capacitor 219, and/or other energy storing circuitry, elements, devices and/or systems, to supplement and/or condition the electrical energy supplied, or obtained, by the ambient energy capture module 212. Similar to the battery 218, the capacitor 219 can store electrical energy from the ambient energy capture module 212 and can discharge the stored electrical energy as needed and/or required for one or more functions/features of the physiological parameter monitoring patch 210.

The physiological parameter monitoring patch 210 can also include a processing module 220 that can include a processor 221 and/or memory 222. The processing module 220 can control one or more functions and/or features of the patch 210 and/or can prepare and/or store collected physiological parameter data for transmission. For example, the processing module 220 can instruct the collection of physiological parameter data according to a schedule and can then store the collected data and/or instruct, or cause, the transmission of the collected data. In this example, the scheduled collection of physiological data can allow the ambient energy capture module 212 to collect and store electrical energy in the energy storage module 217 for use during the physiological data collection.

In another embodiment, the collection of the physiological data can be caused be performed in an "on-demand" basis. That is, a user, an external device and/or an external system, can signal the acquisition and/or transmission of physiological data by the physiological parameter monitoring patch 210. For example, a companion device 250 can broadcast, or transmit, a signal, such as a power signal, to the patch 210 to cause the collection and/or transmission of the physiological data. A user and/or an external device/system can cause the companion device 250 to transmit the signal to cause the collection of the physiological data as needed and/or as requested in the "on-demand" manner.

The processor 221 of the processing module 220, can process the collected physiological data, if sufficient power, or electrical energy, is present in the physiological parameter patch 210 and/or capturable, or obtainable, by the ambient energy capture module 212. For example, the processor 221 can review the collected physiological data to determine if there are indications of a physiological trend, or other indications, of a physiological condition or state. The processor 221 can monitor the physiological data for changes and/or abnormal values and can cause an alert to be transmitted from, or otherwise provided by, the physiological parameter monitoring patch 210 to alert to the condition and/or abnormalities.

The memory 222 can store the collected physiological data and/or operating instructions for the processor 221. The collected physiological data can be stored in the memory 222 and can be transmitted, such as by the communication module 223, at intervals and/or as requested. The processor 221 can access the memory 222 for operating instructions and/or to store physiological parameter data.

The communication module 223 can wirelessly transmit data, such as physiological parameter data, from the physiological parameter monitoring patch 210 to an external device and/or system, such as the companion device 250. The communication module 223 includes a transmitter and/or a transceiver and can use one or more communication protocols, such as Bluetooth®, Wi-Fi, and/or other wireless communication protocols or means. Communication between the communication module 223 and the external device/system can be secured and/or encoded. To assist with the transmission of the data from the communication module 223, the communication module 223 can include, or be coupled to, an antenna through which the data can be transmitted.

In addition to transmission capabilities, the communication module 223 can optionally include reception capabilities. Data and/or other communications can be directed to and/or received by the physiological parameter monitoring patch 210 via the communication module 223. The received data can be directed by the communication module 223 to one or more components of the patch 210, such as the processor 221. The received data can include various information, such as processor instructions regarding the schedule of physiological parameter data collection. Alternative and/or additional information and/or data can be transmitted to the communication module 223 for use by or in one or more functions/features of the patch 210.

The sensor module 224 of the physiological parameter monitoring patch 210 can include one or more sensors 225 to sense and/or collect data regarding a physiological parameter. The sensors can be positioned and/or arranged on the patch 210 to assist with the collection of the physiological data. Example physiological parameters that can be monitored by one or more sensors 225 of the sensor module 224 can include oxygen saturation ($SpO_2$), pH, temperature, blood pressure (invasive and/or non-invasive), electrocardiogram (ECG), impedance and/or other physiological parameters. Sensors 225 can also include sensors to monitor the position and/or orientation of the wearer of the patch. The sensor 225 generates an output, such as data, indicative of the monitored physiological parameter. This output, or data, can be collected and/or transmitted by the communication module 223 to the companion device 250 for monitoring the physiological state of the wearer of the patch. The sensors 225 can be designed and/or selected for low power operation so as to reduce the electrical energy requirement of the sensor 225. The reduced power requirement can reduce the amount of electrical energy the ambient energy capture module 212 has to supply, which can also reduce the size and/or complexity of the module 212.

In an example, the sensor 225 can include a communication capability to allow the sensor to transmit the physiological data directly, such as by short-range broadcasting the data to a nearby device and/or system, such as the companion device 250. Transmitting the physiological parameter data directly from the sensor 225 and/or sensor module 224 can bypass the communication module 223 which can reduce the electrical energy requirement of the physiological parameter monitoring patch 210.

The companion device 250 can generate and/or radiate/transmit energy that can be captured, or obtained, by the ambient energy capture module 212 of the physiological parameter monitoring patch 210 and/or can receive the physiological data from the patch 210. The companion device can include a communication module 251, a processing module 252, a location module 255, a power module 257, and/or an input/output module 258. The companion device 250 can process the received physiological data and can transmit the data and/or other information derived therefrom, such as a report, to an external device and/or system. For example, the companion device 250 can be a device placed near or on a wearer of the physiological parameter monitoring patch 210, to provide a power supply for the patch 210 and to receive and/or process the collected physiological data. Additionally, the companion device 210, and/or its features/functions, can be integrated with one or more devices and/or systems that may be positioned near a wearer to interact with the patch 210. In an example embodiment, the functions and/or features of the companion device 250 can be integrated into existing devices, such as cellular phone and/or other medical devices.

The communication module 251 of the companion device 250 can communicate with the physiological parameter monitoring patch 210 to receive physiological data and/or transmit data/instructions thereto. Multiple physiological parameter monitoring patches 210 can be communicating with the communication module 251 to transmit data regarding one or more physiological parameters of the wearer of the patches 210. This can allow a single companion device 250 to be assigned to a wearer to monitor one or more of their physiological parameters.

The communication module 251 can communicate with other external devices and/or systems to transmit the physiological data, processed and/or raw, and other information derived and/or based on the physiological data. Communication by the communication module 251 with an external device/system, other than the patch 210, can be via a wired and/or a wireless connection using one or more communication protocols. For example, the companion device 250 can communicate with a patient monitoring and/or tracking system to update patient information to include the collected physiological data. The companion device 250 can include various rules and/or instructions regarding the routing of the physiological information, or data based thereon, such as transmitting an alert to a device, system and/or user based on the physiological data. For example, the communication module 251 can establish a first communication pathway to transmit first collected physiological parameter data to a first medical device and a second communication pathway to transmit second collected physiological parameter data to a second medical device. In this manner, the communication module 251 can transmit the relevant physiological parameter data to a particular medical device(s), systems and/or users. For example, relevant physiological parameter data can be transmitted from the companion device 250 to a patient monitor/defibrillator and the same, or different, relevant physiological parameter data can be transmitted to a nursing station.

Additionally, the communication module 251 can communicate with other medical devices and/or system that are monitoring various physiological parameters/characteristics of the wearer of the physiological parameter monitoring patch 210. The companion device 250 can use this additional received physiological data to assist with making determinations based on the sensed physiological data received from the patch 210 and/or assist with processing the received physiological data. For example, a scale can provide weight information regarding the wearer of the patch to the companion device 250. This weight data can be used in processing and/or monitoring the physiological data received from the patch 210 and in the determination of abnormalities and/or wearer distress indicated by the received physiological data.

The processing module 252 can include a processor 253 and/or memory 254. The processor 253 can control various functions and/or features of the companion device 250 and/or can process the received physiological parameter data. The memory 254 can store information, such as the received physiological parameter data, and can store instructions for the processer 253 to perform or execute. For example, the processor 253 can process the received physiological parameter data from the physiological parameter monitoring patch 210. The physiological parameter data can be processed to determine trends, abnormal values and/or other information regarding the physiological parameter(s) monitored. Based on the processing of the physiological data, the processor 253 can instruct the transmittal of the physiological data, or portion thereof, to an external device, system and/or user, and/or the transmittal of other information or notifications based on the processed physiological parameter data. Notifications can include alerts or alarms, such as contacting emergency services, regarding physiological parameter data indicating a patient distress condition. The alert/alarm, and or other physiological data, can be transmitted to multiple locations to disseminate the information to the relevant parties, devices and/or systems in a timely manner. In addition, the alerts/alarms and/or physiological data can be routed, such as based on rules and/or determinations made by the processor, external device/system, to various location in preparation for potential treatment and/or movement of the wearer of the physiological parameter monitoring patch 210 in response to the received physiological parameter data.

The optional location module 255 can include elements, devices and/or systems for determining the location of the companion device 250. For example, the location module 255 can include a GPS sensor/receiver 256 to receive/determine GPS coordinate information regarding the location of the companion device 250. In an example embodiment the wearer of the physiological parameter monitoring patch 210 can be in distress and the distress can be determined by the companion device 250 based on the received physiological data from the patch 210. In response to the determined distress, the companion device 250 can transmit an alert or notification for assistance for the wearer, the alert or notification can include location information from the location module 255. In this manner, the wearer is not relied upon to supply the location information, which wearers may be unable to do depending on their condition. Additional, or alternative, location determination elements, devices and/or systems can be included in the location module 255 to assist with determining location of the companion device 250.

A power module 257 of the companion device 250 can provide and/or assist with providing power, such as electrical energy, to the companion device 250. For example, the power module can include a plug to connect the companion device 250 to an external power source, such as a wall socket. Additionally, the power module 257 can include one or more energy storage devices that can store electrical energy to allow the companion device 250 to function for a period of time absent a connection to an external power source. For example, the power module 257 can include batteries, such as rechargeable batteries, that can provide electrical energy to the various functions and/or features of the companion device 250.

In addition, and/or alternatively, the power module 257 can provide the ambient energy from which the physiological parameter monitoring patch 210 can extract, or obtain, energy therefrom. For example, the power module 257 can broadcast radio transmissions that can be received by the patch 210 to generate electrical energy from the radio 213 energy. The transmitted radio energy 213 by the power module 257 can have specific characteristics/properties, or ranges thereof, such as frequency, wavelength, amplitude, etc. The characteristics/properties of the power module transmitted radio transmissions can be based on the reception properties of the patch 210, such as to have an increased efficiency of the conversion of the radio transmission energy to electrical energy by the patch 210.

In an example embodiment, the power transmission via radio waves by the power module 257 can be in conjunction with one or more communication protocol transmissions so that the companion device 250 is transmitting both power and data across a specific radio spectrum. Alternatively, to assist with reducing potential interference, the spectrums used for power transmission and communication can be separate from each other.

The input/output module 258 can include visual 259 and/or audio 262 based input/output. The input/output module 258 can relay information to the wearer of the companion device 250 and/or patch 210 and/or another user. The information can include the physiological data sensed by the patch 210, or data/information derived therefrom, information regarding the operation/functions of the patch 210 and/or companion device 250 and/or other information. In addition to relaying information, the input/output module 258 can also receive input, such as from a user or other. This input can alter the operation of the companion device 250 and/or cause the companion device 250 to perform one or more functions/features in response to the received input.

The visual 259 of the input/output module 258 can include a display 260 and/or touchscreen/keyboard 261. The display 260 can be coupled to one or more functions/features of the companion device 250, such as the processing module 252, to display information. The display can be a digital or analog display to relay various information to a user or other. The touchscreen/keyboard 261 can provide a visual input for a user or other to provide input to the companion device 250. The keyboard can be a physical device with various actuatable elements, such as keys, that can be manipulated by the user or other to provide the input. The touchscreen can be both an input device and an output device, whereas the display 260 is typically only an output device. The touchscreen 261 can display information, such as prompts, that a user or other can interact with to provide input to the companion device 250. In an embodiment, the touchscreen 261 can include keyboard-like functionality to allow a user or other to provide input to the companion device 250.

The audio 262 of the input/output module 258 can include a microphone 263 and/or a speaker 264. The microphone 263 can allow a user or other to provide an audio input to the companion device 250. The audio input can include verbal, or voice, commands that can be processed by the input/output module 258 to cause the companion device 250 to perform a task. For example, a user can use the audio input provided by the microphone 263 to query the companion device for information, such as physiological data collected, or received, from the physiological parameter monitoring patch 210. This can allow the user to input information, such as a request, in a hands-free manner.

The speaker 264 can provide an audible output for the companion device 250 to relay information to a user and/or other. The speaker can be coupled to the processing module 252 and/or other features/functions of the companion device 250 to relay information therefrom. Information relayed by the speaker 264 can include physiological data and/or information derived from or based thereon, alarms/alerts and/or other audio outputs.

Figure 3:
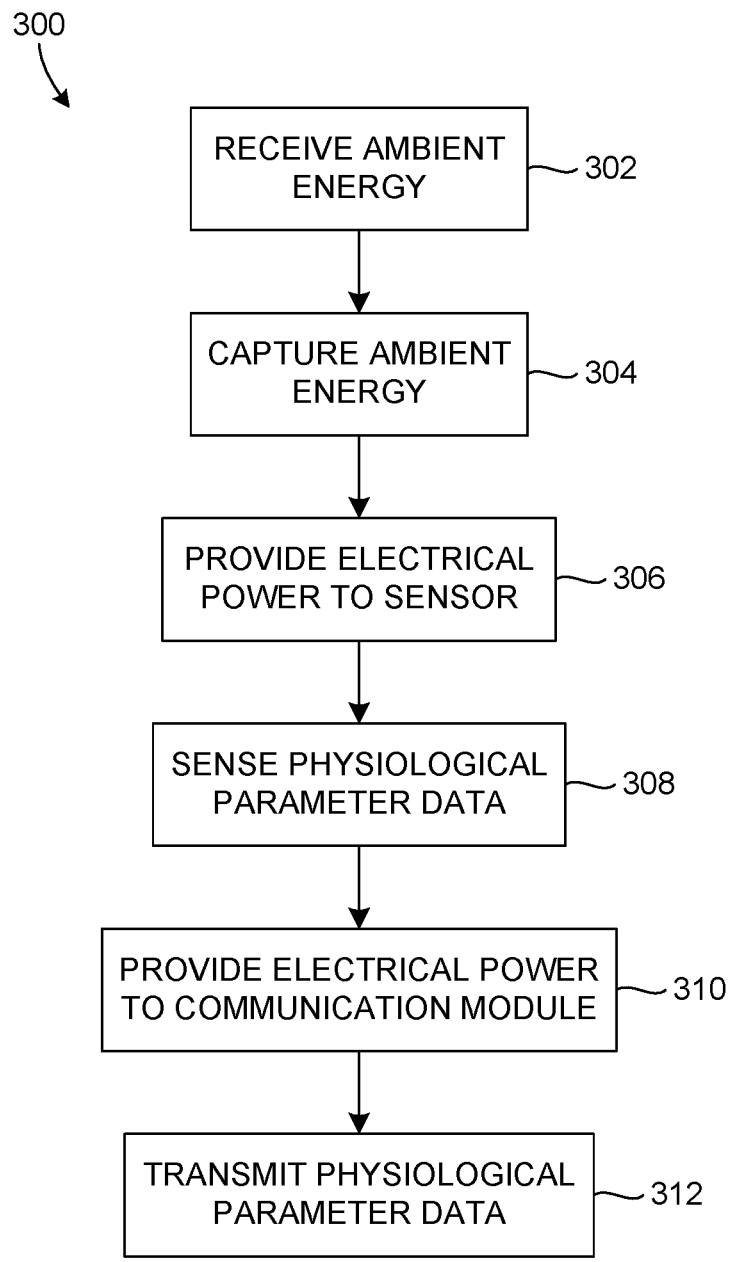
FIG. 3 illustrates an example ambient energy powered physiological parameter monitoring method.

FIG. 3 is an example method 300 of ambient energy powered physiological parameter monitoring. At 302 ambient energy, from a surrounding environment, is received and captured at 304. The ambient energy can be created, transmitted and/or broadcasted for the specific purposed of being received 302, and/or can be energy from a source that is otherwise radiating and/or broadcasting energy intentionally or unintentionally. For example, a device can transmit ambient energy to be received 302 and captured 304 and/or the ambient energy can be from source that is radiating the ambient energy as part of, or as a byproduct, of one or more functions/features of the source, or its operation, such as wireless communication signals. The capture 304 of the ambient energy can include the use of the captured ambient energy to create electrical energy. One or more elements, devices and/or systems can capture the ambient energy and generate electrical energy as a result of the ambient energy capture 304.

At 306, the electrical energy, or power, is provided to a sensor. The sensor can be an element, device and/or system for sensing data regarding one or more physiological parameters. The sensor can be included on a patch, or other element, that can be placed on, or affixed to, a person to monitor the physiological parameter and generate data therefrom. At 308, the sensor senses the physiological parameter data and can generate a signal that can be output, the signal being representative and/or based on the sensed physiological parameter data.

At 310 electrical power, such as from the ambient energy capture 304, can be provided to a communication module. The communication module can wirelessly transmit 312 the physiological parameter data to a remote device, system and/or user. Various communication protocols, systems and/or devices can be used to transmit the physiological parameter data.

Figure 4:
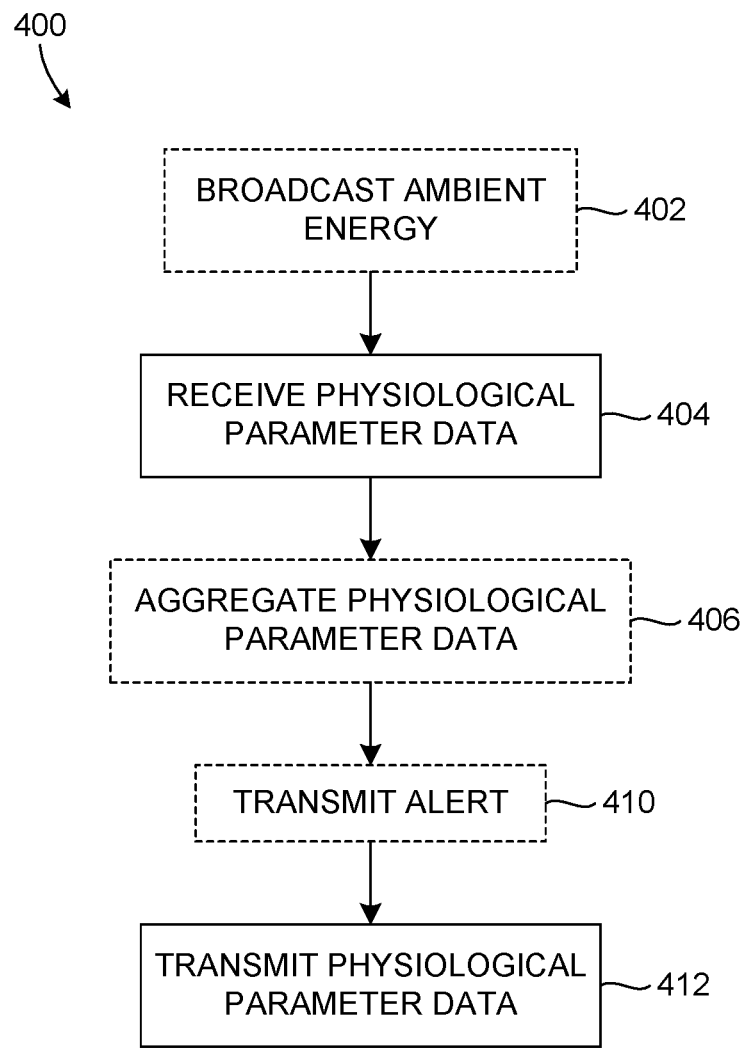
FIG. 4 illustrates an example method of receiving physiological parameter data from an ambient energy powered physiological parameter monitoring system.

FIG. 4 is an example method 400 of receiving physiological parameter data from an ambient energy powered physiological parameter monitoring system. At 402, ambient energy can be broadcasted and/or transmitted wirelessly to allow another remote device and/or system, such as a physiological parameter monitoring patch, to generate, or capture, electrical energy from the ambient energy. A device and/or system, such as a companion device, can interact with the remote device/system to provide a source of electrical energy and/or receive data transmission from the remote device/system. The ambient energy can be received by the remote device/system to provide the electrical energy for the remote device/system to sense data regarding one or more physiological parameters. The sensed data can then be transmitted by the remote device/system and received at 404 as physiological parameter data. The transmission of the physiological parameter data can be in response to the broadcast of ambient energy 402 and/or otherwise caused/triggered, such as by a schedule or other signal.

Multiple physiological parameter data can be received 404 from one or more remote devices/systems, such as the physiological parameter monitoring patch. The received physiological data 404 can be aggregated and/or processed 406. Various determinations and/or analyses can be made based on the received physiological parameter data 404 and/or the aggregated/processed physiological data 406. For example, comparisons of the physiological parameter data to trends and/or threshold can be used to determine if an alert should be transmitted 410 in response to the received physiological data 404 and/or the aggregated/processed physiological data 406. The alert can be transmitted 410 to one or more remote devices, systems and/or users to inform them of physiological data.

At 412, the physiological data, such as 404 and/or the aggregated/processed data 406, can be transmitted to a remote device, system and/or user. The physiological data transmitted can be raw and/or processed sensor data and/or determination, evaluations and/or analyses made therefrom. The transmission 412 can include transmitting the received physiological data to another device and/or system, such as a hub, that can process received physiological and/or other patient data to evaluate a physiological state of the patient being monitored and/or perform one or more functions and/or actions in response to the received, transmitted physiological data.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing the invention in diverse forms thereof.

The invention claimed is:

1. A system comprising:
   a patch comprising:
      an antenna configured to harvest electrical energy from an electromagnetic field generated by an external energy source;
      a sensor configured to sense a patient physiological parameter, wherein the sensor is configured to be powered by the electrical energy; and
      a transceiver configured to transmit data representing the patient physiological parameter, wherein the transceiver is configured to be powered by the electrical energy; and
   a companion device configured to receive the data transmitted from the transceiver and to store the data.

2. The system of claim 1, wherein the patch further comprises a patch energy source configured to power the sensor, and wherein the sensor is further configured to sense the patient physiological parameter when the sensor is powered by the patch energy source.

3. The system of claim 2, wherein the patch energy source comprises a battery.

4. The system of claim 1, wherein the companion device is further configured to transmit the data representing the patient physiological parameter to a remote device.

5. The system of claim 1, wherein the companion device or the transceiver is further configured to transmit the data representing the patient physiological parameter to an external device that is electrically connected to the patch by a short-range electrical field.

6. The system of claim 1, wherein the companion device is further configured to send instructions to the patch to schedule a transmission of the data representing the patient physiological parameter.

7. The system of claim 1, wherein the patch is wearable by a patient.

8. The system of claim 1, wherein the patch is a first patch, and the system further comprises a second patch comprising:
   a second antenna configured to harvest second electrical energy from the electromagnetic field;
   a second sensor configured to sense a second patient physiological parameter, wherein the second sensor is configured to be powered by the second electrical energy; and
   a second transceiver configured to transmit second data representing the second patient physiological parameter, wherein the second transceiver is configured to be powered by the second electrical energy,
   the companion device further configured to receive the second data transmitted from the second transceiver and to store the second data.

9. The system of claim 8, wherein:
   the electromagnetic field comprises radio transmissions;
   the antenna of the first patch is configured to harvest the electrical energy from first radio transmissions of a first frequency; and
   the second antenna of the second patch is configured to harvest the second electrical energy from second radio transmissions of a second frequency different than the first frequency.

10. The system of claim 1, wherein the companion device further comprises a location module that is configured to determine the location of the patch and to transmit the location to a remote device.

11. The system of claim 1, wherein the companion device is further configured to transmit the data representing the patient physiological parameter to a remote server over a wireless network.

12. The system of claim 1, wherein the companion device is electrically coupled to the patch.

13. The system of claim 1, wherein the patch further comprises an energy storage device configured to store the electrical energy as stored electrical energy, and wherein the sensor and the transceiver are configured to be powered by the stored electrical energy.

14. The system of claim 1, wherein the sensor is further configured to initiate sensing of the patient physiological parameter in response to the antenna harvesting the electrical energy from the electromagnetic field.

15. A patch comprising:
   an antenna configured to harvest electrical energy from an electromagnetic field generated by an external energy source;
   an energy storage device configured to store the electrical energy as stored electrical energy;
   a sensor configured to sense a patient physiological parameter, wherein the sensor is configured to be powered by the stored electrical energy; and
   a transceiver configured to transmit data representing the patient physiological parameter, wherein the transceiver is configured to be powered by the stored electrical energy.

16. The patch of claim 15, wherein the sensor is further configured to initiate sensing of the patient physiological parameter in response to the antenna harvesting the electrical energy from the electromagnetic field.

17. The patch of claim 15, wherein the external energy source is a companion device that is configured to receive the data transmitted from the transceiver.

18. The patch of claim 15, wherein:
   the electromagnetic field comprises radio transmissions within a particular range of frequencies; and
   the patch is configured to harvest the electrical energy from the radio transmissions.

* * * * *